Feb. 16, 1932. J. E. MARKHAM Plant Pat. 7
PEACH
Filed Sept. 6, 1930
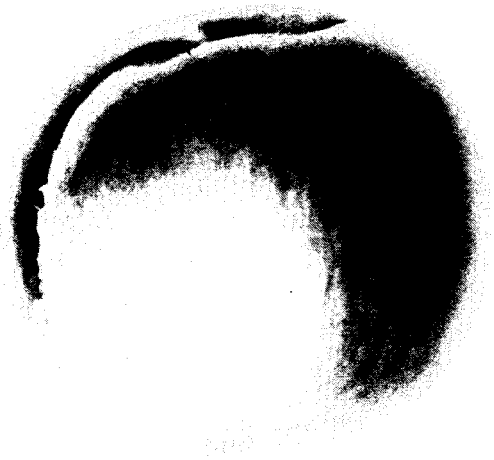
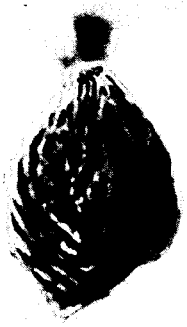
INVENTOR
James E. Markham
By Robb & Robb
ATTORNEYS Patented Feb. 16, 1932

UNITED STATES PATENT OFFICE

JAMES E. MARKHAM, OF XENIA, ILLINOIS, ASSIGNOR TO STARK BRO'S NURSERIES & ORCHARDS COMPANY, OF LOUISIANA, MISSOURI

PEACH

Application filed September 6, 1930. Serial No. 480,220.

The present invention represents improvements in peach trees and the fruit of the same. The new and distinct variety of this peach resulted from a cross of the J. H. Hale peach and an unknown yellow variety of a strong and vigorous character, the object in view being by reproduction to combine and improve the good characteristics of the two varieties so as to obtain a better tree, large in size, bearing good quality fruit and possessing other characteristics which go to make a good commercial or marketable peach.

The annexed drawings and following description set forth the leading characteristics of the new variety which I have asexually reproduced:

*Tree.*—Tree is extraordinarily vigorous, with spreading upright growth and is very hardy. Tree bears very young and produces a heavy crop of uniformly large peaches, exceeding in size and quality those of its progenitors. Trunk and main branches are strongly knit together with wide angle forks. Bark on trunks and branches peculiarly smooth and gray-brown in earlier years. Twigs are moderately stout; bark on new growth bright green with shading of dull crimson on exposed side; internodes short; buds rather small, moderately prominent, leaf scars small and oval.

*Foliage.*—The leaves are exceptionally large and long, approximately 6 inches in length and 1½ inches in width. The form is long-ovate; base acute, distinctly wrinkled for a short distance along mid-rib. The margin is prominently wavy, crenate, with minute glandular barbs or tips. Apex is acuminate; entire leaf distinctly curved toward the twig. Upper surfact is moderately glossy, dark green; under surface lighter green with yellowish tinge; smooth. Scarcely a trace of pubescence is to be found even near the mid-rib, which is light yellowish green and prominent. Stem is short, yellowish green strongly curved. Glands usually two, sometimes three or four, with small or partly developed glands situated on the blade of the leaf, small, reniform.

*Bloom.*—Bloom is small "South China" type. Calyx is medium in size—reddish brown. Calyx cup is yellow. Petals are short, rounded and concave. They are salmon pink or yellowish pink in color. Anthers are pale yellow, numerous, but small and imperfect, producing but little, if any, viable pollen. Filaments are usually much shorter than pistil.

*Fruit.*—The distinctive feature of the fruit of this variety is that it is uniformly large—there being no small peaches appearing upon the trees. In form the peach is globular and averages somewhat over 3 inches in diameter, varying scarcely ¼ inch either way, with an upward range of size to 4 inches. Cavity is rather large, narrow and almost abrupt; suture beginning at the edge of the cavity, well defined but not deeply marked at any point; extending to the apex and slightly beyond. The apex is pointed but depressed to such a degree that the point does not project beyond the periphery. Sides of fruit are slightly unequal, the greatest inequality appearing near one side of the suture line.

The surface of the fruit is smooth; ground color deep lemon yellow to orange practically overspread with mottling and shading of red extending from the orange crimson at the edge of the ground color through various shades to a very deep carmine appearing almost black on the exposed cheek. Pubescence is moderate in amount, short, readily removed, grayish in color; skin thin, but supported by the firm flesh, is not easily injured.

Color of flesh is rich golden yellow, with distinct and rather extensive red coloring about the pit—the red extending outward from the pit in ray-like shadings; flesh texture is firm, fine grained, slightly fibrous, melting when full ripe, very juicy; flavor rich sub-acid, a little sharp until fully mature when a decided sweetness develops; aroma distinct, rich and pleasing. Quality is excellent.

*Seed.*—Stone is perfectly free, medium size in proportion to the volume of the fruit, average length 1½ inches, width 1⅛ inches, thickness ¾ inch; form broadly ovate with distinct point. Color is deep brown with distinct and deep convolutions.

*Ripening season.*—This peach follows the J. H. Hale and Elberta ripening season—ripening about one to two weeks after when grown under comparable conditions.

It is to be understood that the foregoing characteristics are typical but subject perhaps to slight variation which may arise by reason of change of environment.

I claim:

The peach tree herein described, characterized by the lateness of the ripening period of its fruit, as shown.

In testimony whereof I affix my signature.

JAMES E. MARKHAM.